United States Patent [19]

Klein et al.

[11] 4,203,145
[45] May 13, 1980

[54] CHLORO-DIPHENYL

[75] Inventors: Alfons Klein, Duesseldorf; Ernst Knust; Rudolf Kron, both of Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 867,543

[22] Filed: Jan. 6, 1978

[30] Foreign Application Priority Data

Jan. 29, 1977 [DE] Fed. Rep. of Germany ....... 2703745

[51] Int. Cl.$^2$ .............................................. H01B 3/24
[52] U.S. Cl. ........................................ 361/317; 252/65
[58] Field of Search .................. 252/65; 361/317, 318; 174/17 LF; 260/612 R

[56] References Cited

U.S. PATENT DOCUMENTS

| 2,165,813 | 7/1939 | Prutton | 252/65 X |
|---|---|---|---|
| 2,170,782 | 8/1939 | Clark | 252/65 X |
| 2,170,989 | 8/1939 | Coleman et al. | 252/65 X |
| 2,198,473 | 4/1940 | Clark | 252/65 X |
| 3,025,440 | 3/1962 | Martin | 252/65 X |
| 3,072,728 | 1/1963 | Kosmin et al. | 260/612 R |
| 3,755,467 | 8/1973 | Darsow et al. | 252/65 X |
| 4,097,912 | 6/1978 | Lapp et al. | 252/65 X |
| 4,097,913 | 6/1978 | Lapp et al. | 252/65 X |
| 4,115,834 | 9/1978 | Robinson et al. | 252/65 X |

FOREIGN PATENT DOCUMENTS 1468847  3/1977  United Kingdom .

OTHER PUBLICATIONS

Abstract of Belgium Patent 824,984.

Primary Examiner—Harris A. Pitlick
Attorney, Agent, or Firm—Sprung, Felfe, Horn, Lynch & Kramer

[57] ABSTRACT

An improvement in an electrical device containing a functional liquid wherein the functional liquid is a compound of the formula

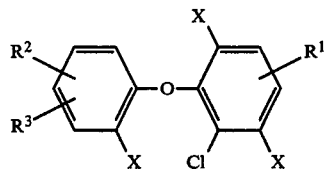

and the use of such compounds as dielectrics.

29 Claims, 2 Drawing Figures

CHLORO-DIPHENYL

BACKGROUND OF THE INVENTION

1. Field of the Invention

The invention relates to liquids, which have dielectric properties and can be employed in electrical devices.

2. Discussion of Prior Art

It is known to use polychlorinated biphenyls as dielectric liquids in capacitors. This class of compounds has found wide industrial use. The poor biological degradability of these compounds, above all of the higher-chlorinated biphenyls, has led to considerable pollution of the environment.

It is also known to use monochlorodiphenyl ether and monochloroalkyldiphenyl ether, containing one or two alkyl groups, as dielectric liquids (DT-OS (German Published Specification) 2,432,160 and DT-OS (German Published Specification) 2,503,799). The dielectric constant of these mixtures is a maximum of 4.9 and does not reach the values of 6.0 of the chlorinated biphenyls hitherto used in practice. For this reason, they cannot be used industrially with satisfaction as substitutes for chlorinated biphenyls.

SUMMARY OF THE INVENTION

Dielectric liquids have been found which comprise one or more compounds of the general formula

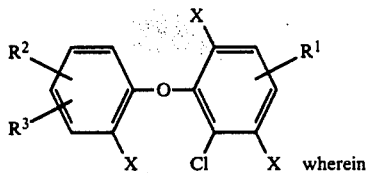

wherein

X denotes a hydrogen or chlorine atom and $R^1$ to $R^3$ are identical or different and denote a hydrogen atom, a straight-chain or branched alkyl radical with 1–6 carbon atoms or a cycloalkyl radical with 5–7 carbon atoms. The dielectric constant of the compounds according to the invention has, at 20° C., a value which is in the range from 5.6 to 11.5, preferably from 5.8 to 8.5.

Compounds of the formula (I) are known and can be prepared by processes which are in themselves known, for example by reacting alkali metal phenolates with halogenoaromatic compounds or reacting alkali metal alkylphenolates with halogenoaromatic compounds (DT-OS (German Published Specification) 2,242,419; and DT-OS (German Published Specification) 1,643,344).

It is, of course, possible subsequently to alkylate or chlorinate a diphenyl ether. For alkylation, the halogenodiphenyl ethers or alkyl-halogenodiphenyl ethers are reacted with olefins in the presence of acid catalysts, such as mineral acids (for example hydrochloric acid, sulphuric acid or phosphoric acid), organic sulphonic acids (for example p-toluenesulphonic acid) or acid-activated Fuller's earths, or with halogenoalkanes in the presence of Friedel-Crafts catalysts.

For example, a chlorination can be carried out in the customary manner with sulphuryl chloride in carbon tetrachloride (J.chem. Soc. London 1950, 1686).

For example, it is possible to alkylate 2-chlorodiphenyl ether with olefins, 1 to 3 alkyl groups being introduced into the molecule. The reaction mixture which forms contains, depending on the amount of olefin used non-alkylated 2-chlorodiphenyl ether and the corresponding mono-, di- and trialkylated compounds. The reaction mixture can be employed as a dielectric without further separation.

The pure compounds can be obtained, for example, by distillation.

Examples of compounds of the formula (I) which may be mentioned are: 2-chloro-diphenyl ether, 2,3-dichloro-diphenyl ether, 2,6-dichloro-diphenyl ether, 2,2'-dichloro-diphenyl ether, 2,6,2'-trichloro-diphenyl ether, 2,3,6-trichlorodiphenyl ether, 2-methyl-2'-chloro-diphenyl ether, 3-methyl-2'-chloro-diphenyl ether, 4-methyl-2'-chloro-diphenyl ether, 2-ethyl-2'-chloro-diphenyl ether, 3-ethyl-2'-chloro-diphenyl ether, 4-ethyl-2'-chloro-diphenyl ether, 2-isopropyl-2'-chlorodiphenyl ether, 3-isopropyl-2'-chloro-diphenyl ether, 4-isopropyl-2'-chloro-diphenyl ether, 2-sec.-butyl-2'-chlorodiphenyl ether, 3-sec.-butyl-2'-chloro-diphenyl ether, 4-sec.-butyl-2'-chloro-diphenyl ether, 2-tert.-butyl-2'-chlorodiphenyl ether, 3-tert.-butyl-2'-chloro-diphenyl ether, 4-tert.-butyl-2'-chloro-diphenyl ether, 2-cyclopentyl-2'-chlorodiphenyl ether, 3-cyclopentyl-2'-chloro-diphenyl ether, 4-cyclopentyl-2'-chloro-diphenyl ether, 2,4-dimethyl-2'-chlorodiphenyl ether, 2,4-diisopropyl-2'-chloro-diphenyl ether, 2,4-di-sec.-butyl-2'-chloro-diphenyl ether, 2,4-di-tert.-butyl-2'-chloro-diphenyl ether, 4,4'-dimethyl-2'-chloro-diphenyl ether, 4,5'-dimethyl-2'-chloro-diphenyl ether, 2,4'-dimethyl-2'-chloro-diphenyl ether, 2,5'-dimethyl-2'-chloro-diphenyl ether, 4-mthyl-2',3'-dichloro-diphenyl ether, 2-methyl-2',3'-dichloro-diphenyl ether, 4,4'-dimethyl-2,2'-dichloro-diphenyl ether, 4,4'-di-tert.-butyl-2'-chloro-diphenyl ether, 4-methyl-2',6'-dichlorodiphenyl ether, 3-methyl-2',6'-dichloro-diphenyl ether, 2-methyl-2',6'-dichloro-diphenyl ether, 4-methyl-2-chloro-diphenyl ether, 5-methyl-5-chloro-diphenyl ether, 3-methyl-2',3',6'-trichloro-diphenyl ether, 4,4'-dimethyl-2',3'-dichloro-diphenyl ether, 4,3'-dimethyl-2',6'-dichlorodiphenyl ether, 3,4'-dimethyl-2',3'-dichloro-diphenyl ether, 3,3'-dimethyl-2',6'-dichlorophenyl ether, 2,4'-dimethyl-2',6'-dichlorodiphenyl ether and 2,3'-dimethyl-2',6'-dichlorodiphenyl ether.

DESCRIPTION OF SPECIFIC EMBODIMENTS

Figure 1:
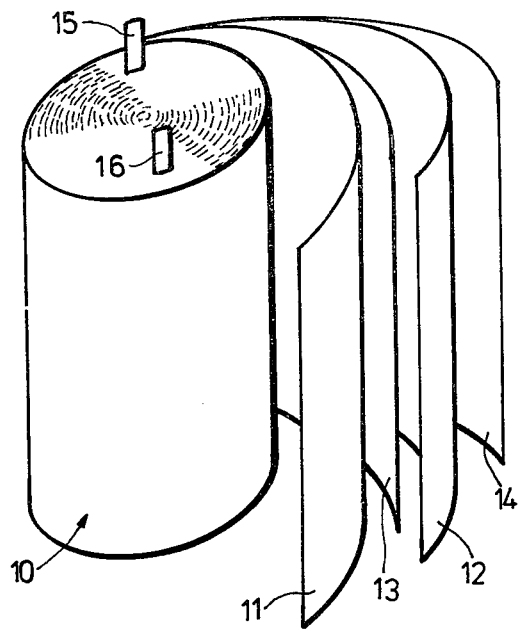

The dielectric liquids according to the invention, which contain the compounds of the formula

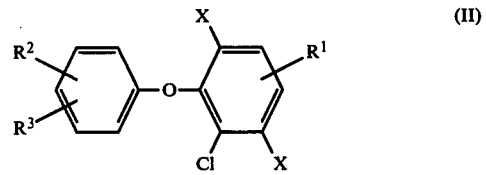

wherein $R^1$, $R^2$, $R^3$ and X have the abovementioned meaning, are distinguished by a higher dielectric constant than comparable isomers.

In particular, the following dielectric liquids according to the invention may be mentioned:

(a) 2-methyl-2'-chloro-diphenyl ether,
(b) the isomer mixture, containing compounds of the formula (I), which is formed in the reaction of 3,4-dichlorotoluene with sodium phenolate, (c) the isomer mixture, containing compounds of the formula (I), which is formed in the reaction of 3,4-dichlorotoluene with sodium cresolate (o, m or p), (d) the isomer mixture, containing compounds of the formula (I), which is formed in the reaction of one mol of 2-chlorodiphenyl ether with one mol of propylene, (e) the isomer mixture, containing compounds of the formula (I), which is formed in the reaction of one mol of 2-chlorodiphenyl ether with one mol of n-butene and (f) the isomer mixture, containing compounds of the formula (I), which is formed in the reaction of 2,3,4-trichloro-toluene with sodium phenolate.

The compounds of the formula (I) can be used individually or in mixtures. In order to achieve a low pour point, it can be appropriate to employ isomer mixtures.

It is, of course, possible for the dielectric liquids according to the invention to contain further components. For example, compounds can be added which react with the impurities in the dielectric, which are formed during the functioning of the capacitor, and thus extend the life of the capacitor.

Customary additives are, for example, epoxide compounds (DT-OS (German Published Specification) 2,503,799, page 11), which can be employed individually or in mixtures. The following epoxide compounds may be mentioned as examples: 1,2-epoxy-3-phenoxypropane, bis-(3,4-epoxy-6-methylcyclohexylmethyl) adipate, 1-epoxy-ethyl-3,4-epoxy-cyclohexane, 3,4-epoxy-cyclohexylmethyl-3,4-cyclohexanecarboxylate, 3,4-epoxy-6-methylcyclohexylmethyl-3,4-epoxy-6-methylcyclohexanecarboxylate and 2,2-bis-(4-hydroxyphenyl)-propane diglycidyl ether.

In general, 0.1 to 5% by weight, preferably 0.3 to 1% by weight, of the epoxide compound is added, relative to the total amount of the dielectric liquid.

One can, of course mix the dielectric liquids according to the invention with customary dielectrics, such as mineral oils, diphenyl ether, polychloroaromatic compounds or alkyldiphenyl ethers. In this manner one can establish a particular dielectric constant.

If the dielectric liquids according to the invention are in the form of a mixture, they essentially contain compounds of the formula (I). In general, a proportion of more than 60% by weight of the compounds of the formula (I) in the functional liquid is preferred. A proportion of 80 to 100% by weight of the compounds of the formula I in the functional liquid is particularly preferred.

The invention also relates to the use of the compositions according to the invention, containing compounds of the formula (I), as a dielectric, in particular as impregnating agents for electrical devices. Electrical devices which may be mentioned are, in particular, capacitors and transformers. Capacitors having a structure consisting of multi-layer paper and aluminium foil, of metallised paper, of a metallised plastic film, for example of polypropylene or polyterephthalic acid ester, or of a mixed dielectric, for example of paper, plastic film and aluminium foil or of metallised paper and plastic film, may be mentioned in particular.

Electric capacitors which contain the halogenated diphenyl oxides of the invention can be prepared and impregnated according to customary processes. Such capacitors display a low loss factor, a high capacity, long life, good low temperature performance, resistance to fire and excellent biological degradability of the impregnation agent as such.

In the accompanying drawings

Figure 2:
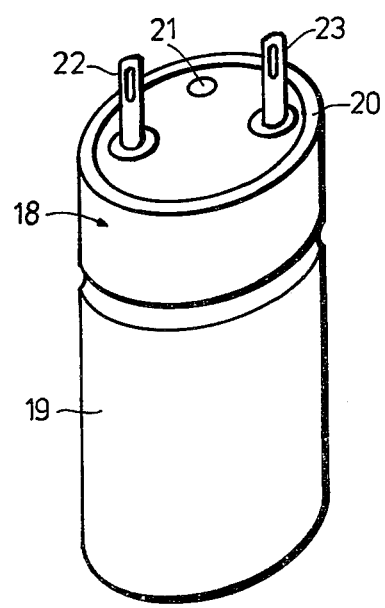

FIG. 1 shows a perspective view of a partially wound capacitor reel as subject of the present invention and FIG. 2 a perspective view of a completely assembled capacitor which contains the capacitor part, comprising plates wound on top of each other, of the type shown in FIG. 1, together with a dielectric liquid impregnation agent.

The capacitors used according to the present invention have the general structure and composition illustrated in FIG. 1, that is, a capacitor 10 with the plates wound on top of each other in the form of a roll, the capacitor containing separated electrode foils or armatures 11 and 12 and intermediarily arranged separators 13 and 14. The connecting elements 15 and 16 have enlarged surfaces (not shown) which are in contact with the electrode foils 11 and 12. The electrode foils 11 and 12 can contain one or more different materials, generally metals, including for example aluminium, copper and stainless steel. The dielectric separators 13 and 14 generally contain paper and/or a polymer film. The dielectric separator 13 and the metal electrode foils 11 and 12 thus together form a capacitor element. The materials of the dielectric separators and the hollow spaces in and between the materials and the electrode foils are impregnated with a dielectric liquid.

With further reference to FIG. 1 of the illustration, the dielectric separators 13 and 14 consist of a solid, flexible, porous material, such as highly-refined cellulose paper, or an essentially non-porous polymer film, such as polyolefine, or a combination of paper and polymer film. In a preferred embodiment the paper material is preferably a two- or multilayered power-capacitor paper, the thickness of each individual layer being not greater than approx. 0.025 mm and preferably approx. 0.0076 mm, and the total thickness being such as is appropriate for the intended potential of the capacitor. This type of paper has relatively good dielectric stability in comparison with the dielectric stability of other dielectric materials and it exhibits a relatively high dielectric constant. The polymer material is preferably a biaxially-orientated polypropylene film, although other materials related to the polyolefin group, especially polyethylene and 4-methyl 1-pentene, have also been employed to a certain extent for capacitor purposes. Other suitable polymer materials included polyester, polyvinylidene fluoride and polysulphone. Although the paper or the polymer film can be used alone, combinations of these two are often used. The paper is arranged next to the polymer film in such a way that is serves as a kind of wick to bring the dielectric liquid impregnation agent into the area corresponding to the contact area between the porous paper and the essentially non-porous polymer material.

With reference to FIG. 2, an assembled capacitor unit 18 is illustrated, which encloses a capacitor with plates wound on top of each other, of the type explained in FIG. 1. The assembled unit consists of a container 19, a hermetically sealed cover 20 including a small hole 21 for drying the reel and for inserting the dielectric liquid and a pair of connecting terminals 22 and 23 which extend through the cover 20 and which are insulated against this. The connecting terminals 22 and 23 are connected inside the container 19 with the end connecting elements 15 and 16, as shown in FIG. 1. Although not illustrated, the unit 18 indicated in FIG. 2 further encloses the liquid dielectric preparation which fills the remaining space in the container 19 not taken up by the capacitor element and which further impregnates the dielectric separators 13 and 14.

The impregnation of the capacitor is effected according to conventional processes. For example, the capacitor units enclosed in containers, such as the capacitor 18 of FIG. 2, are dried in vacuo to remove residual moisture, according to a generally customary process. The drying temperature will vary according to the length of drying time, but will usually be in the region of approx. 60° to 150° C. At too low temperatures the drying time is excessively long, whereas too high temperatures can cause decomposition of the paper or shrinkage of the polymer film, which are used as dielectric separators. The hole 21 enables moisture and gases to escape from the inside of the container 19 during the drying process.

The impregnating dielectric liquid is applied to the capacitor arrangement through the hole 21, preferably for as long as the dried arrangement is still under vacuum in a suitable vacuum chamber. The capacitor element must be immersed in the impregnation agent inside the container and usually sufficient impregnation liquid is introduced so that the container is completely filled. The pressure of the chamber is then raised to atmospheric pressure and the arrangement is left to stand for several hours or is left to become completely immersed, in order to enable thorough penetration of the liquid impregnation agent. Following impregnation the capacitor unit can be closed by applying an appropriate amount of solder or any other sealing composition on to the hole 21. The capacitor arrangement can then be subjected to elevated temperatures, in order to raise the pressure within the capacitor arrangement.

The relative wettability of the solid separating material as well as the viscosity of the impregnation agent are favourably influenced by heat and pressure; the increase in pressure further produces a more rapid penetration of the impregnation agent into the intermediate spaces of the dielectric separating material.

In general, the compositions according to the invention can be prepared by bringing the components together. In general, the compounds of the formula (I) are purified before being employed as a dielectric. The purification can be carried out in the customary manner (Chem. Industrie, 9, 526 (1966)), for example by a treatment with Fuller's earth or aluminium oxide.

It is surprising that the alkyl-chloro-diphenyl ethers in the dielectric liquids according to the invention, which have at least one chlorine substituent in the ortho-position to the ether oxygen, have particularly outstanding electrical properties, in particular a high dielectric constant.

Thus it can be seen from DT-OS (German Published Specification) 2,432,160, that the positions of the substituents on the aryl nuclei of the monochloro-alkyl-diphenyl ethers listed there are of minor importance for the dielectric properties of these compounds.

Dielectrics which are to be used for the impregnation of capacitors advantageously have a dielectric constant between about 4 and about 6, since the electrical loss is still low in this range (Industrial Chemicals as Alternative Dielectric Fluids, Power Engineering Society, 1974, Intermeeting, Paper No. C74-765-5). Dielectrics with a high dielectric constant can be employed in combinations with additives which lower the dielectric constant. It is particularly advantageous when the dielectrics have a dielectric constant which is equal to or a little higher than 6. This advantage is particularly well fulfilled by the dielectrics according to the invention.

The optimum dielectric constant can be easily established by combination with additives. This is particularly advantageous, since the dielectric constant of the dielectric liquid should not be smaller than the dielectric constant of the solid dielectric, in order to achieve a distribution of potential which is as uniform as possible and a high dielectric strength. The optimum dielectric constant for capacitor paper, of 6.2 can be particularly easily achieved with the aid of the dielectrics according to the invention.

In addition to the advantageous electrical properties of the compositions according to the invention, the good biological degradability and the low toxicity are to be singled out in particular.

The dielectrics according to the invention virtually do not decompose during use. Thus, during use, advantageously, virtually no acid decomposition products form. This has the result that virtually no corrosion is caused by the dielectrics according to the invention.

EXAMPLES

(A) Preparation of the dielectrics

EXAMPLE 1

A mixture of 2,352 g of 1,2-dichlorobenzene (16 mols), 432 g of a cresol mixture (4 mols) consisting of 70% of 3-cresol and 30% of 4-cresol, 80 g of sodium hydroxide (2 mols) and 11.2 g of potassium hydroxide (0.2 mol) is heated to the boil, whilst stirring, and the water formed (about 40 ml) is distilled off azeotropically. 2 g of copper-II oxide (0.025 mol) are then added and the mixture is stirred for a further 7 hours at 150° C.

The reaction mixture is cooled and washed with water. In a subsequent vacuum distillation, the unreacted 1,2-dichloro-benzene and the cresol are first separated off. 367 g of an isomer mixture consisting of 2-chloro-3'-methyl- and 2-chloro-4'-methyl-diphenyl ether are obtained at a boiling point$_{15}$ of 165°–168° C.

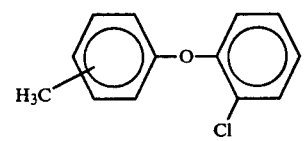

Relative permittivity (Er) (20° C.): 7.2.

EXAMPLES 2–9

The dielectrics according to Examples 2–9 are prepared in an analogous manner to Example 1.

| Example No. | Starting compounds | Dielectric | Boiling point |
|---|---|---|---|
| 2 | 2-methyl-phenol and 1,2-dichlorobenzene | 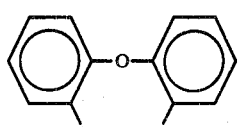<br>Er: (20° C.) = 6.7 | 161° C./12 mm Hg |
| 3 | 4-tert.-butylphenol and 1,2-dichlorobenzene | 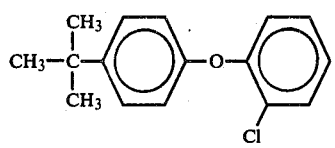<br>Er: (20° C.) = 6.15 | 189°–191° C./12 mm Hg |
| 4 | 4-isopropylphenol and 1,2-dichlorobenzene | 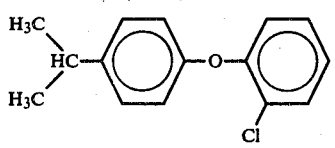<br>Er: (20° C.) = 6.5 | 137°–144° C./1.4 mm Hg |
| 5 | 2-tert.-butylphenol and 1,2-dichlorobenzene | 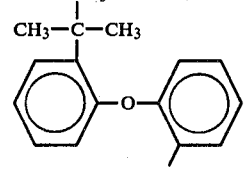<br>Er: (20° C.) = 5.3 | 172°–177° C./8 mm Hg |
| 6 | mixture: 70% of 3-cresol, 30% of 4-cresol and 3,4-dichlorotoluene | 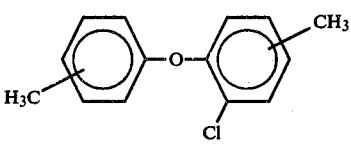<br>Er: (20° C.) = 7.3 | 120°–124° C./0.4 mm Hg |
| 7 | 4-tert.-butylphenol and 3,4-dichlorotoluene | 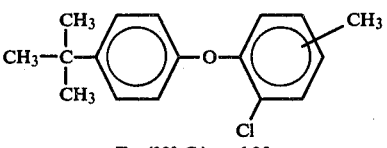<br>Er: (20° C.) = 6.25 | 138°–140° C./0.5 mm Hg |
| 8 | 2-cresol and 3,4-dichlorotoluene | 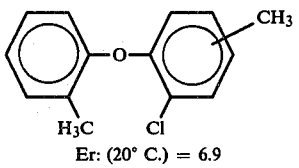<br>Er: (20° C.) = 6.9 | 113°–128° C./0.7 mm Hg |
| 9 | phenol and 3,4-dichlorotoluene | 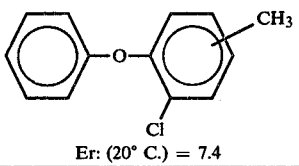<br>Er: (20° C.) = 7.4 | 111°–115° C./0.5 mm Hg |

EXAMPLE 10

A mixture of 259 g of a cresol mixture (2.4 mols) consisting of 70% of 3-cresol and 30% of 4-cresol, 1.8 l of dimethylsulphoxide, 0.3 l of toluene and 135 g of potassium hydroxide (2.4 mols) is heated to the boil, whilst stirring, and the water of reaction formed is distilled off azeotropically during this procedure.

The mixture is cooled and 436 g of 1,2,3-trichlorobenzene (2.4 mols) are added and the mixture is boiled for 5 hours. Potassium chloride precipitates during the reaction.

After the reaction has ended and the mixture cooled, the reaction mixture is poured into 8 l of water and the organic phase is separated off and washed with water. The reaction mixture thus obtained is subjected to fractional distillation; unreacted cresol and 1,2,3-trichlorobenzene are first obtained. 310 g of an isomer mixture consisting of

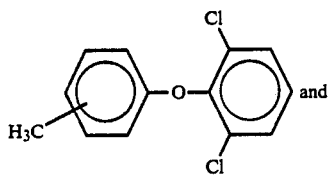

and

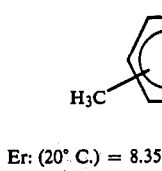

Er: (20° C.) = 8.35 are obtained at a boiling point$_{15}$ of 182°–190° C.

EXAMPLE 11

The following isomer mixture is obtained from phenol and 1,2,3-trichlorobenzene by the manner described in Example 10:

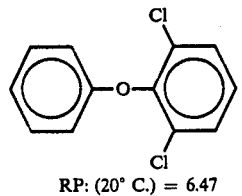

RP: (20° C.) = 6.47

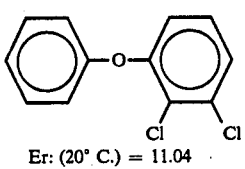

Er: (20° C.) = 11.04

After distilling this isomer mixture over a 1 m packed column, 2,6-dichloro-diphenyl ether is obtained at a boiling point$_{0.5}$ of 114°–115° C. and 2,3-dichloro-diphenyl ether is obtained at a boiling point$_{0.5}$ of 123°–126° C.

EXAMPLE 12

The following isomer mixture is prepared from a cresol mixture, consisting of 70% of 3-cresol and 30% of 4-cresol, and 2,3,4-trichloro-toluene in the manner described in Example 10:

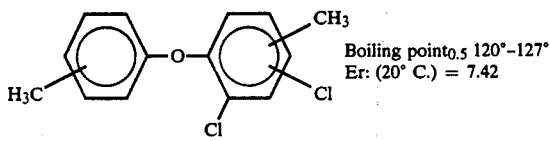

Boiling point$_{0.5}$ 120°–127°
Er: (20° C.) = 7.42

EXAMPLE 13

1,636 g of 2-chloro-diphenyl ether (8 mols) and 80 g of acid-activated Fuller's earth are initially introduced in a flask. 510 g of gaseous propylene are passed in at 130° C., whilst stirring.

After the reaction has ended, the reaction mixture is filtered at 100° C. in order to separate off the Fuller's earth. The reaction mixture is subjected to fractional distillation.

The following isomer mixtures are obtained:

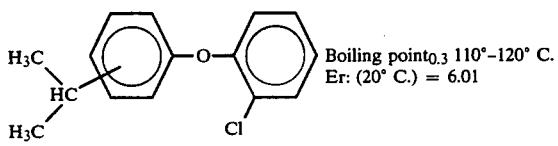

Boiling point$_{0.3}$ 110°–120° C.
Er: (20° C.) = 6.01

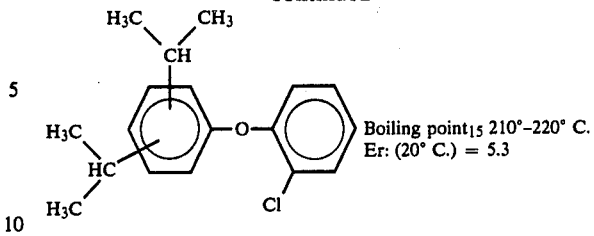

Boiling point$_{15}$ 210°–220° C.
Er: (20° C.) = 5.3

EXAMPLE 14

320 g of gaseous n-butene (5.7 mols) is passed into a mixture of 1,000 g (4.89 mols) of 2-chloro-diphenyl ether and 50 g of acid-activated Fuller's earth at 130° C. After the reaction has ended, the Fuller's earth is separated off by filtration and the filtrate is subjected to fractional distillation in vacuo. The following isomer mixture is obtained:

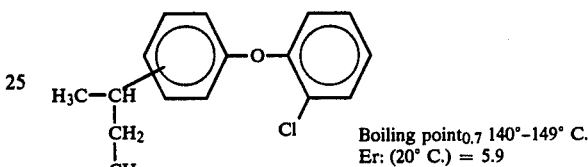

Boiling point$_{0.7}$ 140°–149° C.
Er: (20° C.) = 5.9

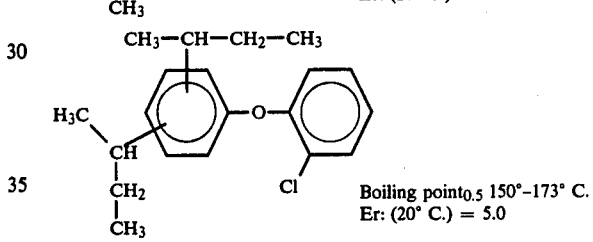

Boiling point$_{0.5}$ 150°–173° C.
Er: (20° C.) = 5.0

EXAMPLE 15

237 g of cyclopentene (3.9 mols) are added dropwise to a mixture of 716 g of 2-chloro-diphenyl ether (3.5 mols) and 56 g of acid-activated Fuller's earth at 130° C., whilst stirring. After the reaction has ended, the Fuller's earth is filtered off and the filtrate is distilled in vacuo. 306 g of the following isomer mixture

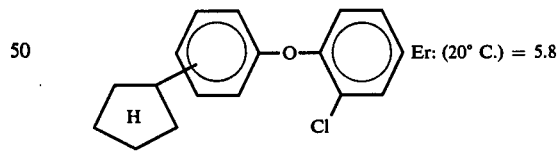

Er: (20° C.) = 5.8 are obtained at a boiling point$_{0.9}$ of 148°–190° C.

EXAMPLE 16

710 g of chlorine (10 mols) are passed into a mixture of 892 g of 4,4'-dimethyl-diphenyl ether (4.5 mols) and 4.5 g of antimony pentachloride at 80° C., whilst stirring. After the reaction has ended, air is passed through the reaction mixture for 3 hours at 50° C., in order to remove the hydrogen chloride which has formed. 50 g of calcium hydroxide are then added and the mixture is heated at 180° C. for 5 hours, whilst stirring. The reaction mixture is distilled under a high vacuum in order to separate off inorganic constituents. Fractional distillation of the reaction mixture then gives 151.2 g of 2-chloro-4,4'-dimethyl-diphenyl ether

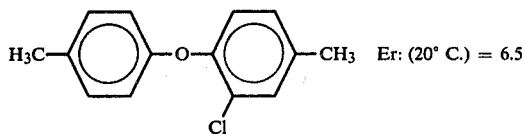 Er: (20° C.) = 6.5 at a boiling point$_{0.7}$ of 131°–135° C. and 214.2 g of 2,2'-dichloro-4,4'-dimethyl-diphenyl ether

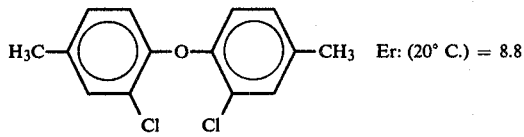 Er: (20° C.) = 8.8 at a boiling point$_{0.4}$ of 137°–145° C.

B Testing the Dielectrics (1) Table 1 shows the test results of a dielectric liquid according to the invention, with dielectric properties, which was prepared according to Example A2.

(2) Table 1 shows the test results of a dielectric liquid according to the invention, with dielectric properties, which was formed by the propylation of 2-chloro-diphenyl ether and has the following composition:

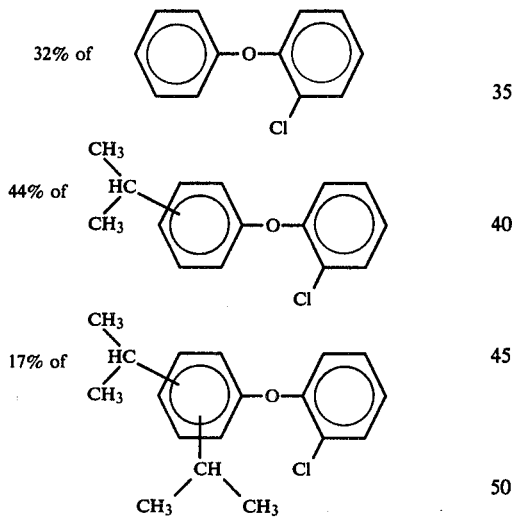

32% of

44% of

17% of

7% of (3) Table 2 shows the test results of a dielectric liquid according to the invention which was formed by the butylation of 2-chloro-diphenyl ether and has the following composition:

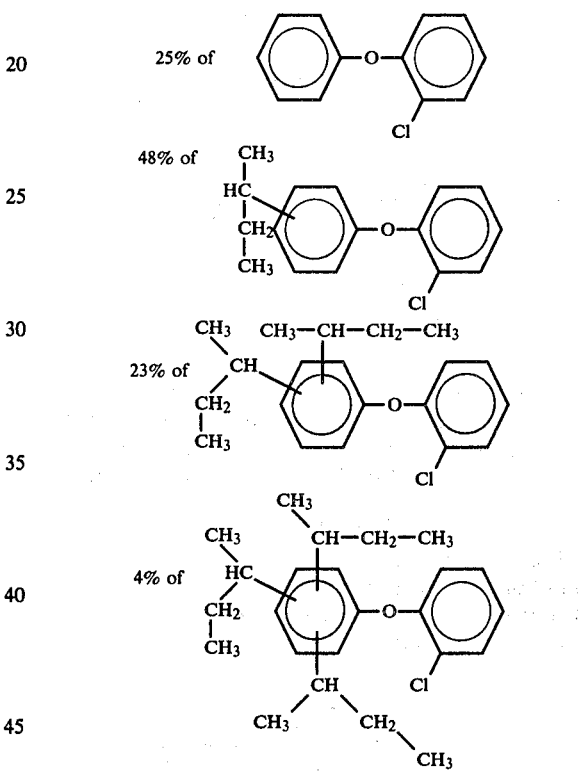

25% of

48% of

23% of

4% of (4) The dielectric properties of a dielectric liquid according to the invention which is formed by mixing 50% of a reaction product of sodium phenolate and 3,4-dichlorotoluene and 50% of a reaction product of sodium phenolate and 2,4-dichlorotoluene were tested. Table 2 shows the results of this test.

Table 1

| Physical constants of the dielectrics according to Example B 1 and 2 | | | | |
|---|---|---|---|---|
| | Test specification | Dimension | B 1 | B 2 |
| consistency | — | — | liquid | liquid |
| colour | ASTM 2,129 | — | colourless | colourless |
| density at 20° C. | DIN 51,757 | kg/m$^3$ | 1163 | 1124 |
| refractive index at 20° C. | DIN 53,491 | — | 1.5840 | 1.5708 |
| viscosity at 20° C. | DIN 51,561 | mm$^2$/s | 10 | 17 |
| pour point | DIN 51,583 | °C. | −45 | −41 |
| neutralisation number | DIN 51,558 | mg KOH/g | <0.01 | 0.017 |
| breakdown voltage | DIN 53,481 | kV | >50 | >50 |
| volume resistivity at 90° C. | DIN 53,482 | GΩ · m | >10 | >100 |
| dissipation factor at 90° C. and 50 Hz | DIN 53,481 | — | 0.006 | 0.005 |
| relative permittivity $\epsilon_r$ | | | | |

Table 1-continued
Physical constants of the dielectrics according to Example B 1 and 2

| | Test specification | Dimension | B 1 | B 2 |
|---|---|---|---|---|
| at 20° C. and 50 Hz | | — | 6.7 | 6.3 |
| at 90° C. and 50 Hz | DIN 53,483 | — | 5.4 | 4.9 |

Table 2
Physical constants of the dielectrics according to Example B 3 and 4

| | Test specification | Dimension | B 3 | B 4 |
|---|---|---|---|---|
| consistency | — | — | liquid | liquid |
| colour | ASTM 2,129 | — | colourless | colourless |
| density at 20° C. | DIN 51,757 | kg/m$^3$ | 1104 | 1167 |
| refractive index at 20° C. | DIN 53,491 | — | 1.5639 | 1.5852 |
| viscosity at 20° C. | DIN 51,561 | mm$^2$/s | 24 | 8 |
| pour point | DIN 51,583 | °C. | −39 | −52 |
| neutralisation number | DIN 51,558 | mg KOH/g | 0.02 | 0.01 |
| breakdown voltage | DIN 53,481 | kV | >50 | >50 |
| volume resistivity at 90° C. | DIN 53,482 | GΩ · m | >100 | >100 |
| dissipation factor at 90° C. and 50 Hz | DIN 53,481 | — | 0.005 | 0.017 |
| relative permittivity $\epsilon_r$ | | | | |
| at 20° C. and 50 Hz | | — | 5.9 | 6.0 |
| at 90° C. and 50 Hz | DIN 53,483 | — | 4.7 | 5.0 |

What is claimed is:

1. In an electrical device containing a dielectric liquid, the improvement wherein said dielectric liquid is a compound of the formula

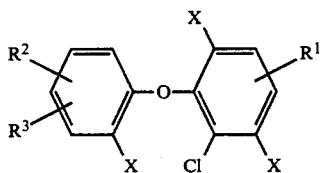

wherein
X=Cl or H;
R$^1$ and R$^3$ are independently C$_{1-6}$ alkyl or C$_{5-7}$ cycloalkyl or hydrogen; and
R$^2$ is C$_{1-6}$ alkyl or C$_{5-7}$ cycloalkyl.

2. An electrical device according to claim 1 wherein said compound has the formula

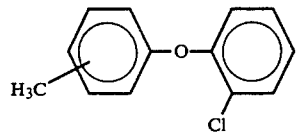

3. An electrical device according to claim 1 wherein said compound has the formula

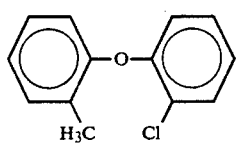

4. An electrical device according to claim 1 wherein said compound has the formula

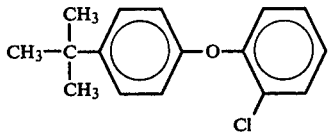

5. An electrical device according to claim 1 wherein said compound has the formula

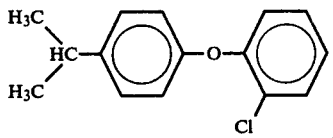

6. An electrical device according to claim 1 wherein said compound has the formula

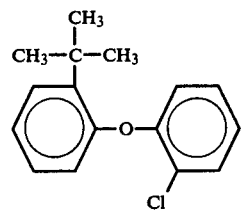

7. An electrical device according to claim 1 wherein said compound has the formula

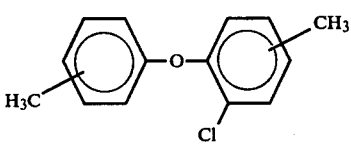

8. An electrical device according to claim 1 wherein said compound has the formula

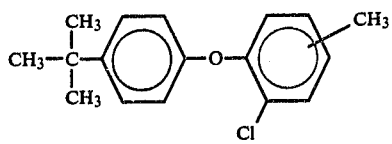

9. An electrical device according to claim 1 wherein said compound has the formula

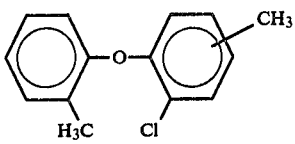

10. An electrical device according to claim 1 wherein said compound has the formula

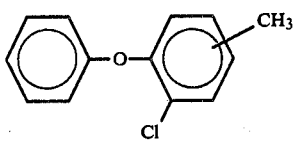

11. An electrical device according to claim 1 wherein said compound has the formula

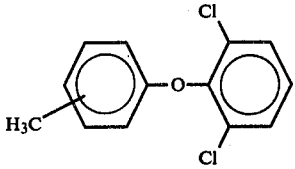

12. An electrical device according to claim 1 wherein said compound has the formula

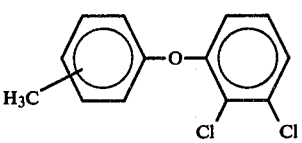

13. An electrical device according to claim 1 wherein the compound is 2,3-dichloro-diphenyl ether.

14. An electrical device according to claim 1 wherein said compound has the formula

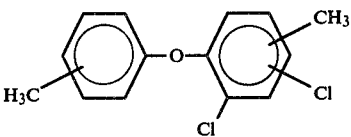

15. An electrical device according to claim 1 wherein said compound has the formula

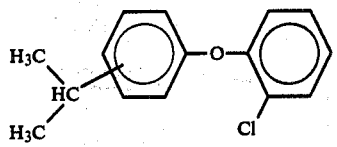

16. An electrical device according to claim 1 wherein said compound has the formula

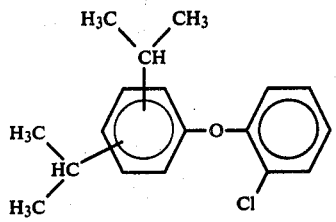

17. An electrical device according to claim 1 wherein said compound has the formula

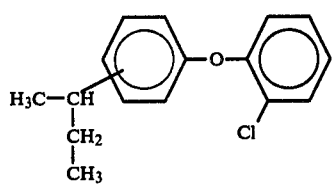

18. An electrical device according to claim 1 wherein said compound has the formula

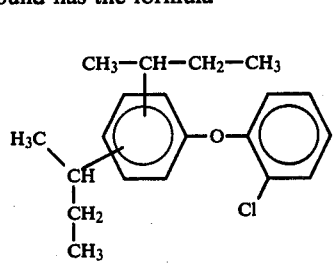

19. An electrical device according to claim 1 wherein said compound has the formula

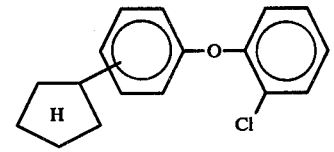

20. An electrical device according to claim 1 wherein said compound has the formula

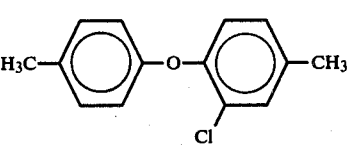

21. An electrical device according to claim 1 wherein said compound has the formula

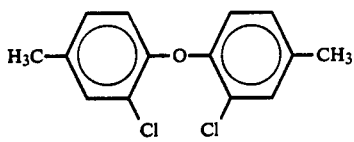

22. An electrical device according to claim 1 which is a capacitor.

23. A capacitor according to claim 22 comprising a plurality of sheets spaced apart, said capacitor having between the sheets said dielectric liquid.

24. A capacitor according to claim 23 comprising a plurality of sheets in the form of electrode foils wound about each other and separated by separators.

25. A capacitor according to claim 24 wherein said separators are impregnated with said dielectric liquid.

26. A capacitor according to claim 25 wherein said separators are composed of paper or a polymeric film.

27. A capacitor according to claim 26 wherein said separators are porous, solid and flexible.

28. A capacitor according to claim 22 wherein said dielectric liquid is a mixture of compounds having the formula

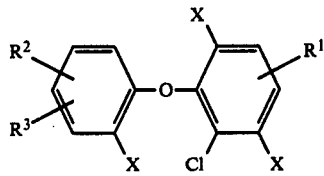

wherein
X denotes a hydrogen or chlorine atom
$R^1$ and $R^3$ independently represent $C_{1-6}$ alkyl, $C_{5-7}$ cycloalkyl or hydrogen and
$R^2$ represents $C_{1-6}$ alkyl or $C_{5-7}$ cycloalkyl.

29. A capacitor according to claim 28 wherein said mixture of dielectric liquids is made by alkylation of 2-chlorodiphenylether with an olefin such that the resultant mixture of functional liquids contains mono-, di- and trialkylated 2-chlorodiphenylether.

* * * * *

UNITED STATES PATENT AND TRADEMARK OFFICE
CERTIFICATE OF CORRECTION

PATENT NO. : 4,203,145
DATED : May 13, 1980
INVENTOR(S) : ALFONS KLEIN, ERNST KNUST, RUDOLF KRON, and KARLFRIED WEDEMEYER It is certified that error appears in the above–identified patent and that said Letters Patent are hereby corrected as shown below:

| Column | Line | |
|---|---|---|
| 2 | 32 | "mthyl" should be --methyl--. |
| 2 | 38 | "5-chloro" should be --2-chloro--. |

Signed and Sealed this

Fifth Day of August 1980

[SEAL]

Attest:

SIDNEY A. DIAMOND

Attesting Officer

Commissioner of Patents and Trademarks